United States Patent
Kondo et al.

(10) Patent No.: US 11,840,489 B2
(45) Date of Patent: Dec. 12, 2023

(54) SYMBIOSIS-PROMOTING AGENT AND METHOD FOR PROMOTING SYMBIOSIS OF ARBUSCULAR MYCORRHIZAL FUNGI

(71) Applicants: Satoshi Kondo, Miyoshi (JP); Madoka Abe, Nagoya (JP); Naoya Takeda, Sanda (JP); Akira Akamatsu, Sanda (JP); Sachi Shimbo, Sanda (JP)

(72) Inventors: Satoshi Kondo, Miyoshi (JP); Madoka Abe, Nagoya (JP); Naoya Takeda, Sanda (JP); Akira Akamatsu, Sanda (JP); Sachi Shimbo, Sanda (JP)

(73) Assignees: TOYOTA JIDOSHA KABUSHIKI KAISHA, Toyota (JP); KWANSEI GAKUIN EDUCATIONAL FOUNDATION, Nishinomiya (JP)

( * ) Notice: Subject to any disclaimer, the term of this patent is extended or adjusted under 35 U.S.C. 154(b) by 269 days.

(21) Appl. No.: 17/218,442

(22) Filed: Mar. 31, 2021

(65) Prior Publication Data
US 2021/0309581 A1    Oct. 7, 2021

(30) Foreign Application Priority Data

Apr. 1, 2020   (JP) .................................. 2020-065939

(51) Int. Cl.
| | |
|---|---|
| *C05C 11/00* | (2006.01) |
| *C05F 11/08* | (2006.01) |
| *A61K 38/06* | (2006.01) |
| *A61K 38/05* | (2006.01) |

(52) U.S. Cl.
CPC ............. *C05C 11/00* (2013.01); *A61K 38/05* (2013.01); *A61K 38/063* (2013.01); *C05F 11/08* (2013.01)

(58) Field of Classification Search
None
See application file for complete search history.

(56) References Cited

U.S. PATENT DOCUMENTS

| | | | |
|---|---|---|---|
| 8,999,888 B2 | 4/2015 | Ogawa et al. | |
| 2014/0194371 A1* | 7/2014 | Mouri | A61P 39/02 514/21.8 |
| 2017/0333518 A1* | 11/2017 | Uekita | C05G 5/40 |
| 2018/0127326 A1* | 5/2018 | Mouri | C05G 1/00 |
| 2019/0153463 A1 | 5/2019 | Turano | |
| 2019/0337864 A1* | 11/2019 | Asada | C05F 11/10 |
| 2019/0382660 A1* | 12/2019 | Shah | C05F 11/00 |
| 2020/0024203 A1* | 1/2020 | Selkirk, Jr. | C05F 11/00 |

(Continued)

FOREIGN PATENT DOCUMENTS

| | | |
|---|---|---|
| CN | 101557709 A | 10/2009 |
| CN | 108392680 A | 8/2018 |

(Continued)

OTHER PUBLICATIONS

Charpentier, M., et al., "Abscisic Acid Promotion of Arbuscular Mycorrhizal Colonization Requires a Component of the Protein Phosphatase 2A Complex 1[W][OPEN]", Plant Physiology, Dec. 2014, vol. 166, pp. 2077-2090.

*Primary Examiner* — Wayne A Langel
(74) *Attorney, Agent, or Firm* — Dinsmore & Shohl LLP (57) ABSTRACT

The present disclosure is intended to enhance the capability for arbuscular mycorrhizal symbiosis by treating the arbuscular mycorrhizal fungi with oxidized glutathione or cystathionine.

9 Claims, 7 Drawing Sheets

(56) References Cited

U.S. PATENT DOCUMENTS

| | | | | |
|---|---|---|---|---|
| 2020/0165244 A1* | 5/2020 | Shioda | ................ | C07D 401/12 |
| 2020/0275667 A1* | 9/2020 | Tanoue | .................... | C05G 5/12 |
| 2020/0308073 A1* | 10/2020 | Devisetty | ............... | A01N 63/22 |
| 2021/0024433 A1* | 1/2021 | Asada | ...................... | C05G 5/10 |
| 2022/0030878 A1* | 2/2022 | Zorner | ................... | A01G 20/00 |

FOREIGN PATENT DOCUMENTS

| | | | |
|---|---|---|---|
| JP | 2017-038562 A | 2/2017 | |
| JP | 2018-170973 A | 11/2018 | |
| WO | 2016/129512 A1 | 8/2016 | |
| WO | 2019/078209 A1 | 4/2019 | |

\* cited by examiner

SYMBIOSIS-PROMOTING AGENT AND METHOD FOR PROMOTING SYMBIOSIS OF ARBUSCULAR MYCORRHIZAL FUNGI

CROSS REFERENCE TO RELATED APPLICATIONS

The present application claims priority from Japanese patent application JP 2020-065939 filed on Apr. 1, 2020, the content of which is hereby incorporated by reference into this application.

BACKGROUND

Technical Field

The present disclosure relates to a symbiosis-promoting agent that acts on arbuscular mycorrhizal fungi that live symbiotically in the roots of plants to improve the symbiotic capability thereof, a method for promoting symbiosis, and a method for plant cultivation.

Background

Arbuscular mycorrhizal fungi are known to live symbiotically in the roots of plants and live symbiotically with approximately 80% of terrestrial plants. Arbuscular mycorrhizal fungi may also be referred to as vesicular-arbuscular mycorrhiza (VA mycorrhiza) because of their structural properties. Arbuscular mycorrhizal fungi encompass approximately 150 special fungal species belonging to the phylum Glomeromycota. When arbuscular mycorrhizal fungi live symbiotically in the roots of plants, they exert functions such as promotion of absorption of nutrients such as phosphorus, improvement of disease resistance, and promotion of moisture absorption. As a result, arbuscular mycorrhizal fungi would exert growth promotion effects on plants with which they live symbiotically. For this reason, use of arbuscular mycorrhizal fungi as a bio-fertilizer can be expected in the field of agriculture.

Arbuscular mycorrhizal fungi are known to promote arbuscule formation upon formation of an abscisic acid-protein phosphatase 2A (PP2A) complex, as described in Plant Physiology, December 2014, Vol. 166, pp. 2077-2090. Specifically, Plant Physiology, December 2014, Vol. 166, pp. 2077-2090 implies that arbuscular mycorrhizal symbiosis may be promoted by allowing abscisic acid to act on plants.

JP 2017-38562 A discloses a method of administering a gibberellin synthesis inhibitor to a plant in an amount for use as a plant growth inhibitor or a smaller amount, so that mycorrhizal symbiosis with plants is promoted. A gibberellin synthesis inhibitor acts on a plant to inhibit synthesis of gibberellin, which is a phytohormone. Thus, mycorrhizal symbiosis can be promoted.

Arbuscular mycorrhizal fungi cannot be cultured in common media and they cannot grow without living symbiotically with plants. As described in JP 2018-170973 A, however, a technique that enables culture of arbuscular mycorrhizal fungi in media supplemented with fatty acid, such as myristic acid or palmitin acid, is known.

SUMMARY

As described above, Plant Physiology, December 2014, Vol. 166, pp. 2077-2090 and JP 2017-38562 A each disclose that a symbiotic promoter is allowed to act on plants to promote arbuscular mycorrhizal symbiosis, although a technique of allowing a symbiotic promoter to act on arbuscular mycorrhizal fungi is not disclosed. While JP 2018-170973 A discloses that fatty acid is allowed to act on arbuscular mycorrhizal fungi, this technique is not intended to enhance the capability for arbuscular mycorrhizal symbiosis.

Under the above circumstances, the present disclosure is intended to provide a symbiosis-promoting agent, which is allowed to act on arbuscular mycorrhizal fungi to enhance the capability for arbuscular mycorrhizal symbiosis with plants, a method for promoting symbiosis, and a method for plant cultivation.

To this end, concentrated studies have been conducted and, as a consequence, it has been discovered that oxidized glutathione or cystathionine may be allowed to act on arbuscular mycorrhizal fungi to enhance the capability for arbuscular mycorrhizal symbiosis to a significant extent. This has led to the completion of the present disclosure.

The present disclosure includes the following.

(1) An agent for promoting symbiosis, which acts on arbuscular mycorrhizal fungi, wherein the agent comprises, as an active ingredient or active ingredients, oxidized glutathione and/or cystathionine.

(2) A method for promoting symbiosis comprising bringing oxidized glutathione and/or cystathionine into contact with arbuscular mycorrhizal fungi.

(3) A microbial material comprising the agent for promoting symbiosis according to (1) and arbuscular mycorrhizal fungi.

(4) A method for plant cultivation comprising allowing arbuscular mycorrhizal fungi treated with oxidized glutathione and/or cystathionine to live symbiotically in roots of the plant to be cultivated.

Advantageous Effects

The agent for promoting symbiosis and the method for promoting symbiosis according to the present disclosure act on arbuscular mycorrhizal fungi to enhance the capability for arbuscular mycorrhizal symbiosis with plants. Thus, the agent for promoting symbiosis and the method for promoting symbiosis according to the present disclosure enable arbuscular mycorrhizal fungi to live symbiotically with plants in an easier manner with higher efficiency, compared with a substance or method that acts on plant roots.

The method for plant cultivation according to the present disclosure involves the use of arbuscular mycorrhizal fungi with an enhanced symbiotic capability. Thus, plant growth promoting effects of arbuscular mycorrhizal fungi can be exerted sufficiently, and growth-promoted plants can be produced.

DETAILED DESCRIPTION

Hereafter, the present disclosure is described in detail.

<An Agent for Promoting Symbiosis>

The agent for promoting symbiosis according to the present disclosure (hereafter, it is simply referred to as "the symbiosis-promoting agent") comprises, as an active ingredient (or active ingredients), oxidized glutathione and/or cystathionine. The agent for promoting symbiosis has functions of acting on arbuscular mycorrhizal fungi to promote hyphal elongation of the arbuscular mycorrhizal fungi. Compared with arbuscular mycorrhizal fungi that are not brought into contact with the symbiosis-promoting agent, the arbuscular mycorrhizal fungi that had been brought into contact with the symbiosis-promoting agent have a significantly enhanced infection rate with plants.

Oxidized glutathione (hereafter, it may be abbreviated to as "GSSG," according to need) has a structure such that two molecules of reduced glutathione (it may be abbreviated to as "GSH," according to need, N—(N-gamma-L-glutamyl-L-cysteinyl)glycine) through disulfide bonding. Oxidized glutathione may bind to other substances (e.g., an acid or base) to form a salt, or it may be contained in the form of a hydrate of such salt or a mixture thereof.

Examples of GSSG salts include, but are not particularly limited to, an ammonium salt, a calcium salt, a magnesium salt, a sodium salt, and a lithium salt. In some certain aspects, the GSSG salt be at least one salt selected from the group consisting of an ammonium salt, a calcium salt, and a magnesium salt.

When the symbiosis-promoting agent is supplemented with GSSG, the GGSG concentration is not particularly limited. For example, it can be 1 microM to 1 mM, including 10 microM to 500 microM, 10 microM to 300 microM, and 10 microM to 100 microM.

Cystathionine is an intermediate of cysteine synthesis, and it is prepared from homocysteine and serine catalyzed by cystathionine beta-synthase. Cystathionine has a structure represented by a chemical formula: $C_7H_{14}N_2O_4S$, which is 2-amino-4-(2-amino-2-carboxy-ethyl)thio-butanoic acid. Cystathionine can be in various forms, such as L-cystathionine, D-cystathionine, cystathionine salt, or a mixture of various forms of cystathionines.

When the symbiosis-promoting agent is supplemented with cystathionine, the cystathionine concentration is not particularly limited. For example, it can be 100 nM to 100 microM, including 500 nM to 10 microM, and 700 nM to 5 microM.

<Arbuscular Mycorrhizal Fungi>

Arbuscular mycorrhizal fungi that have acquired the enhanced symbiotic capability with the aid of the symbiosis-promoting agent are not particularly limited, and all mycorrhizal fungi belonging to the phylum Glomeromycota can be used herein. Specific examples of arbuscular mycorrhizal fungi include fungi that belong to the genera *Rhizophagus*, *Giga-spora*, and *Glomus*. Examples of fungi that belong to the genus *Rhizophagus* include *Rhizophagus arabicus*, *Rhizophagus clarus*, *Rhizophagus custos*, *Rhizophagus diaphanum*, *Rhizophagus fasciculatus*, *Rhizophagus intraradices*, *Rhizophagus iranicus*, *Rhizophagus irregularis*, *Rhizophagus manihotis*, and *Rhizophagus proliferus*.

When arbuscular mycorrhizal fungi adhere to the roots of the target plant of symbiosis in soil, arbuscular mycorrhizal fungi elongate the endophytic hyphae into the roots while passing through the intercellular gap, and they form symbiotic organs referred to as arbuscules inside the plant cells. Arbuscular mycorrhizal fungi spread hyphae inside the roots to supply phosphorus and moisture collected from the soil to plants through the arbuscules while receiving and using the plant photosynthetic product as the energy source.

<Microbial Material>

With the use of the symbiosis-promoting agent and arbuscular mycorrhizal fungi, a microbial material that increases the amount of plant biomass production can be provided. With the use of the microbial material, the target plant to be cultivated can be expected to exert the effects of increased biomass production. The microbial material comprises the symbiosis-promoting agent and arbuscular mycorrhizal fungi described above. In addition, the microbial material can comprise, in addition to the symbiosis-promoting agent and arbuscular mycorrhizal fungi, carriers for such agent for promoting symbiosis and arbuscular mycorrhizal fungi, emulsifying agents, dispersants, anti-foaming agents, adjuvants, and the like.

The microbial material may comprise a single carrier holding the symbiosis-promoting agent and arbuscular mycorrhizal fungi held thereon, or it may comprise a carrier holding the symbiosis-promoting agent and a carrier holding arbuscular mycorrhizal fungi.

Examples of carriers include liquid carriers, such as phosphate buffer, carbonate buffer, and physiological saline. Other examples of carriers include solid carriers, such as natural mineral powders, such as kaolin, clay, talc, bentonite, chalk, quartz, attapulgite, montmorillonite, white carbon, and mineral soil, synthetic mineral powders, such as silicic acid, alumina, and silicate, charcoal, crystalline cellulose, corn starch, gelatin, and alginic acid. Examples of solid carriers that can be used include inorganic substances, such as vermiculite, silica sand, mica, pumice, gypsum, calcium carbonate, dolomite, magnesium, hydrated lime, phosphorus lime, zeolite, and ammonium sulfate. Further examples of solid carriers that can be used include plant organic substances, such as composts, peats, hulls, brans, soy flour, tobacco powders, walnut powders, wheat flours, wood flour, starch, and crystalline cellulose. In addition, examples of solid carriers that can be used include synthetic or naturally-occurring polymeric compounds, such as cumarone resin, petroleum resin, alkyd resin, polyvinyl chloride, polyalkylene glycol, ketone resin, ester gum, gum copal, and gum dammar, wax, such as carnauba wax and yellow wax, and urea.

Examples of adjuvants include anionic surfactants, such as alkyl sulfate esters, alkylsulfate salt, alkylaryl sulfonate salt, and dialkyl sulfosuccinate salt, cationic surfactants, such as salts of higher aliphatic amine, nonionic surfactants, such as polyoxyethyleneglycol alkyl ether, polyoxyethylene glycol acyl ester, polyoxyethylene glycol polyhydric alcohol acyl ester, and cellulose derivatives, thickeners, such as gelatin, casein, and gum Arabic, fillers, and binders.

The microbial material constituted as described above can be in any form of formulations, such as solutions, powders, granules, emulsions, oils, suspending agents, wettable powders, water soluble powders, pastes, capsules, or aerosols.

<A Method for Plant Cultivation>

With the use of the symbiosis-promoting agent described above, the infection rate of arbuscular mycorrhizal fungi with the target plant to be cultivated can be enhanced, and the amount of the plant biomass production can be increased as a consequence. "The use of the symbiosis-promoting agent" encompasses an embodiment in which the symbiosis-promoting agent described above is supplied to soil to treat arbuscular mycorrhizal fungi in the soil with the symbiosis-promoting agent, an embodiment in which arbuscular mycorrhizal fungi treated with the symbiosis-promoting agent described above in advance is supplied to soil, an embodiment in which the microbial material is supplied to soil, and an embodiment in which the symbiosis-promoting agent described above and arbuscular mycorrhizal fungi are supplied to soil.

In any of the embodiments described above, the capability for arbuscular mycorrhizal symbiosis has been enhanced to a significant extent with the use of the symbiosis-promoting agent described above. Thus, the amount of biomass produced from the target plant to be cultivated can be increased. The target plant to be cultivated is not particularly limited, provided that arbuscular mycorrhizal fungi can live symbiotically in the root of such plant. The plant may be a monocotyledonous or dicotyledonous plant, and it may be edible or inedible. Specific examples of monocotyledonous plants include: plants of Amaryllidaceae, such as *Allium fistulosum, Allium cepa, Allium sativum, Allium tuberosum, Allium schoenoprasum* var. *foliosum, Allium bakeri*, and *Allium porrum*; and plants of Gramineae, such as *Oryza sativa, Triticum sativum, Hordeum vulgare, Zea mays*, and *Sorghum bicolor*. Specific examples of dicotyledonous plants include: plants of Leguminosae, such as *Glycine max, Phaseolus vulgaris, Phaseolus angularis, Pisum sativum, Vicia faba, Arachis hypogaea*, clover, *Vigna sinensis*, and *Lotus japonicus*; plants of Rosaceae, such as strawberry; plants of Umbelliferae, such as carrot; plants of Cucurbitaceae, such as cucumber, pumpkin, water melon, and melon; plants of Solanaceae, such as *Solanum melongena, Solanum lycopersicum*, pimento, potato, *Capsicum* annum, Shishito green pepper, and paprika; plants of Malvaceae, such as okra and cotton; and plants of Convolvulaceae, such as sweet potato. Among the plants mentioned above, plants of *Allium*, Leguminosae, Gramineae, and Rosaceae, Amaryllidaceae are options for certain aspects, and *Allium fistulosum, Allium cepa*, strawberry, *Oryza sativa, Triticum sativum, Hordeum vulgare, Lotus japonicus, Glycine max*, and *Zea mays* are further options for other aspects.

A method of supplying the symbiosis-promoting agent or microbial material to soil is not particularly limited. For example, the symbiosis-promoting agent or microbial material can be supplied to soil via spraying, mixing, embedding, instillation, or affusion. When the symbiosis-promoting agent or microbial material is supplied to soil, it may be supplied to part of or the entire soil in which plants are cultivated. Specific examples of places where the symbiosis-promoting agent or microbial material is applied include a planting hole or an area in the vicinity thereof, a planting row or an area in the vicinity thereof, a space between strains, the entire culture soil, the entire soil, a nursery box, a nursery tray, a nursery pot, and a nursery bed.

The symbiosis-promoting agent or microbial material is, in certain aspects, supplied to soil in the form of a solid agent such as granules. By supplying the symbiosis-promoting agent in the form of a solid agent such as granules, the agent can be prevented from flowing out of the soil.

In addition, it is a feature of some aspects that the symbiosis-promoting agent and arbuscular mycorrhizal fungi be together supplied to soil or the microbial material be supplied to soil. Thus, the effects of increased plant biomass production achieved with the aid of arbuscular mycorrhizal fungi can further be enhanced.

The symbiosis-promoting agent or microbial material may be applied to soil either before or after seeding or planting. The timing of application can be, for example, before seeding, the seeding stage, during the period after seeding to budding, the budding stage, the breeding stage, the seedling transplanting stage, the tree cutting or herbaceous cutting stage, the growth stage after settled planting (e.g., before, during, or after flowering, or immediately before or at the time of ear emergence), or at the fruit-coloring stage. The symbiosis-promoting agent or microbial material may be applied to soil only once or a plurality of times. In order to achieve satisfactory effects of plant growth promotion with the use of the symbiosis-promoting agent or microbial material in an amount as small as possible, the symbiosis-promoting agent or microbial material is in some aspects applied before or at the initial stage of plant growth (specifically, during a period from budding to flowering or ear emergence), and it is in further aspects applied before or at the raising of seedling stage.

In an embodiment in which arbuscular mycorrhizal fungi treated with the symbiosis-promoting agent in advance is to be applied to soil, at the outset, arbuscular mycorrhizal fungi are cultured in the presence of the symbiosis-promoting agent. Arbuscular mycorrhizal fungi can be cultured via monoxenic culture with plants to live symbiotically, or arbuscular mycorrhizal fungi can be cultured by themselves.

When arbuscular mycorrhizal fungi are cultured by themselves, for example, culture can be conducted in Modified Melin-Norkrans (MMN) medium. Also, a method involving the use of the MMN medium supplemented with tryptophan dimers or leucylproline (e.g., JP 2009-095332 A) or a method involving the use of porous carriers such as vermiculite or pearlite (e.g., JP 2005-027546 A) can be employed. In addition, a method comprising adding saturated fatty acid having 13 to 18 carbon atoms to a medium can be employed (e.g., JP 2018-170973 A).

A medium used for arbuscular mycorrhizal fungi culture comprises, as base components, assimilable sugar, such as glucose, mannose, xylose, fructose, sucrose, lactose, or raffinose, and inorganic salt, such as sodium hydrogen phosphate. According to need, the medium comprises yeast powder, yeast extract, various vitamins, such as thiamine or pyridoxine, organic nitrogen sources, such as peptone, malt extract, or N-Z Amine (casein enzymatic hydrolysate), pH modifiers, such as inorganic acid, and a base used for preparing a plate medium, such as agar. Examples of known basal media include Hamada medium, modified Hamada medium, Ohta medium, OH medium, and MMN medium. From the viewpoint of spore formation, a medium comprising an organic nitrogen source such as peptone may be selected. The aforementioned components are dissolved in water and then used for culture in the form of a liquid medium or plate medium. A pH level of a medium is modified, according to need. A pH level is on the acidic side at the time of use, and it is 5 to 7 in some aspects. When a plate medium is used, the amount of a base to be added is approximately 1 to 20 mg/ml. A culture method is not different from a common method of mycorrhizal fungi culture. Spores of arbuscular mycorrhizal fungi are inoculated into a medium (either a liquid or plate medium), and culture is conducted at 25 degrees C. to 35 degrees C., and in some aspects at adequate temperature around 28 degrees C. Following culture, hyphae grow from the inoculated spores, new daughter spores are generated from the hyphae, and a large number of sufficiently grown daughter spores are generated.

In order to treat arbuscular mycorrhizal fungi with the symbiosis-promoting agent in advance, for example, the symbiosis-promoting agent may be added to a medium in which arbuscular mycorrhizal fungi are cultured. Alternatively, after arbuscular mycorrhizal fungi are cultured in the medium, a cell suspension may be prepared, and the symbiosis-promoting agent may then be added to the cell suspension. The cultured arbuscular mycorrhizal fungi are treated with the symbiosis-promoting agent by any method, so that the capability for arbuscular mycorrhizal symbiosis can be enhanced.

By enhancing the capability for arbuscular mycorrhizal symbiosis in the manner described above, the infection rate of arbuscular mycorrhizal fungi with plants is enhanced. As a result, effects of increased plant biomass production can be achieved.

When the target plant to be cultivated is treated with a given substance, disadvantageously, it may be necessary to transfer a plant that has been treated with the substance to soil, or the substance that has been supplied to soil may not be able to act on the target plant root. According to the embodiment in which arbuscular mycorrhizal fungi are treated with oxidized glutathione and/or cystathionine described above, in contrast, it is not necessary to transfer the target plant to be cultivated, and the capability for arbuscular mycorrhizal symbiosis can be enhanced in a simple manner.

EXAMPLES

Hereafter, the present disclosure is described in greater detail with reference to the examples, although the technical scope of the present disclosure is not limited to the following examples.

Example 1

In this example, the influence of oxidized glutathione (GSSG) on hyphal elongation of arbuscular mycorrhizal fungi was examined.

The modified M medium (0.3% gerlite, Becard and Fortin, 1988 New phytologist, 108, 211-218) was supplemented with oxidized glutathione (10 microM or 100 microM), spores of arbuscular mycorrhizal fungi (*Rhizophagus irregularis* DAOM197198) were inoculated, and culture was conducted at 30 degrees C. for 4 weeks. For comparison, arbuscular mycorrhizal fungi were cultured in the same manner, except that oxidized glutathione was not added. The number of hyphae elongated outside of the circle (a radius of 7.5 mm) centered on the inoculated portion of the medium was counted, and the extent of elongation was determined based on the number of spores.

Figure 1:
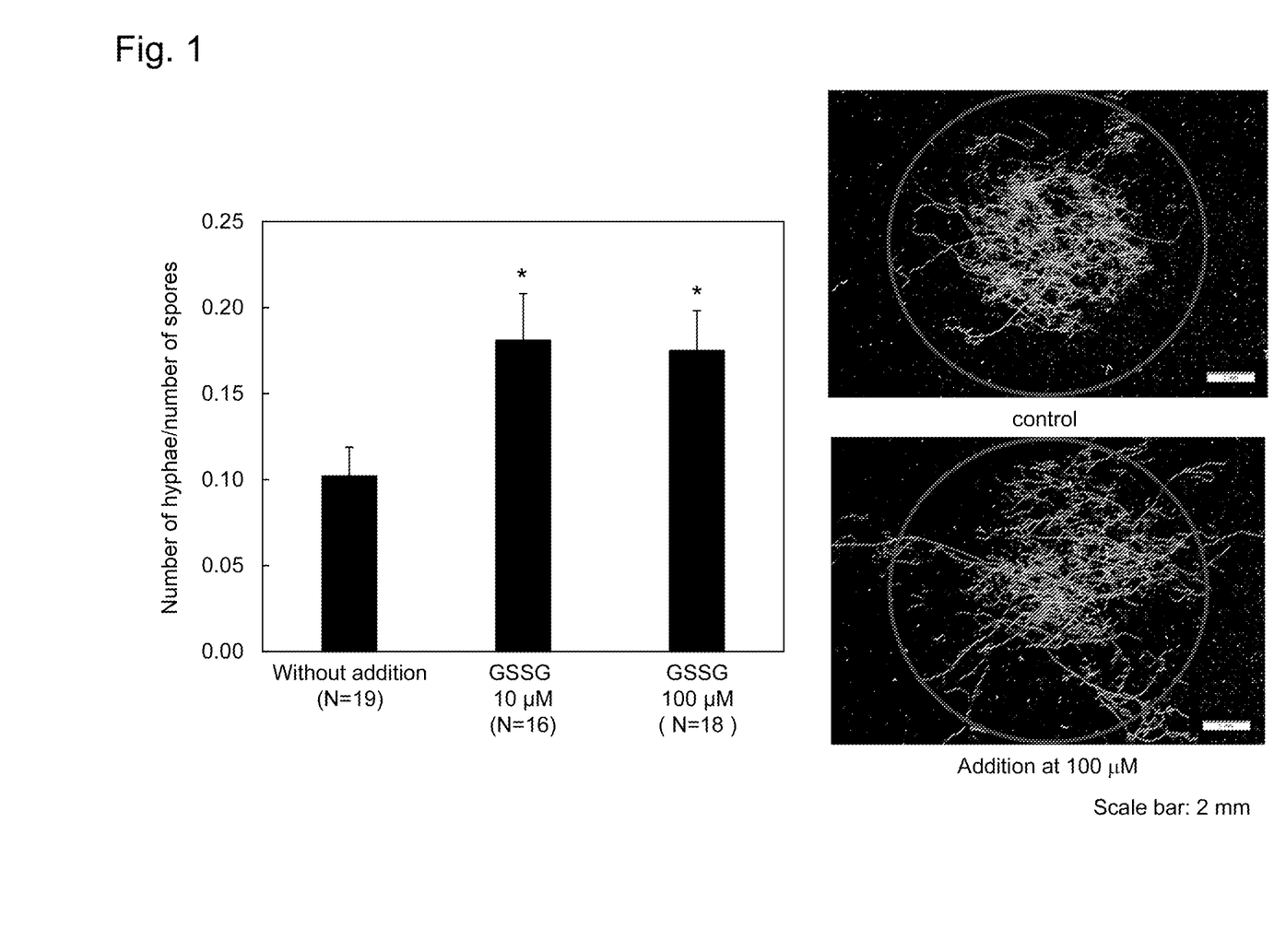
FIG. 1 is a characteristic diagram showing the effects of oxidized glutathione for promoting hyphal elongation of arbuscular mycorrhizal fungi.

The results are shown in FIG. 1. As is apparent from FIG. 1, arbuscular mycorrhizal fungi exerted significant effects of promoting hyphal elongation (*p: less than 0.05, Dunnett's test; n: 16-19), when oxidized glutathione was added at 10 microM or 100 microM, compared with the control (without the addition of oxidized glutathione).

Example 2

In this example, oxidized glutathione was added to soil, dicotyledonous plants were cultivated therein, and the infection rate of arbuscular mycorrhizal fungi was examined.

Specifically, plants of Leguminosae (*Lotus japonicus*) were infected with arbuscular mycorrhizal fungi (*Rhizophagus irregularis* DAOM197198) in soil supplemented with GSSG, and the infection rate (%) of the mycorrhizal fungi invaded inside the roots was determined.

At the outset, the medium (one-tenth of the amount, Hoagland No. 2 basal salt mixture (SIGMA), 0.1 mM $KNO_3$) was added to fertilizer-free soil. Also, control soil supplemented with spores of arbuscular mycorrhizal fungi (4,000 or 6,000 spores) and soil supplemented with spores of arbuscular mycorrhizal fungi (4,000 spores) and GSSG (10 or 100 microM) were prepared. Subsequently, seeds of *Lotus japonicus* (3 days after seeding) that had germinated in agar medium were transplanted therein. The plants were allowed to grow at 23 degrees C. with 16-hour light and 8-hour dark cycles for 4 weeks. Thereafter, *Lotus japonicus* was dug out, the arbuscular mycorrhizal fungi inside the root were stained with ink, and the infection rate of the mycorrhizal fungi (the amount of hyphae per root length (%)) was determined with observation under a microscope.

Figure 2:
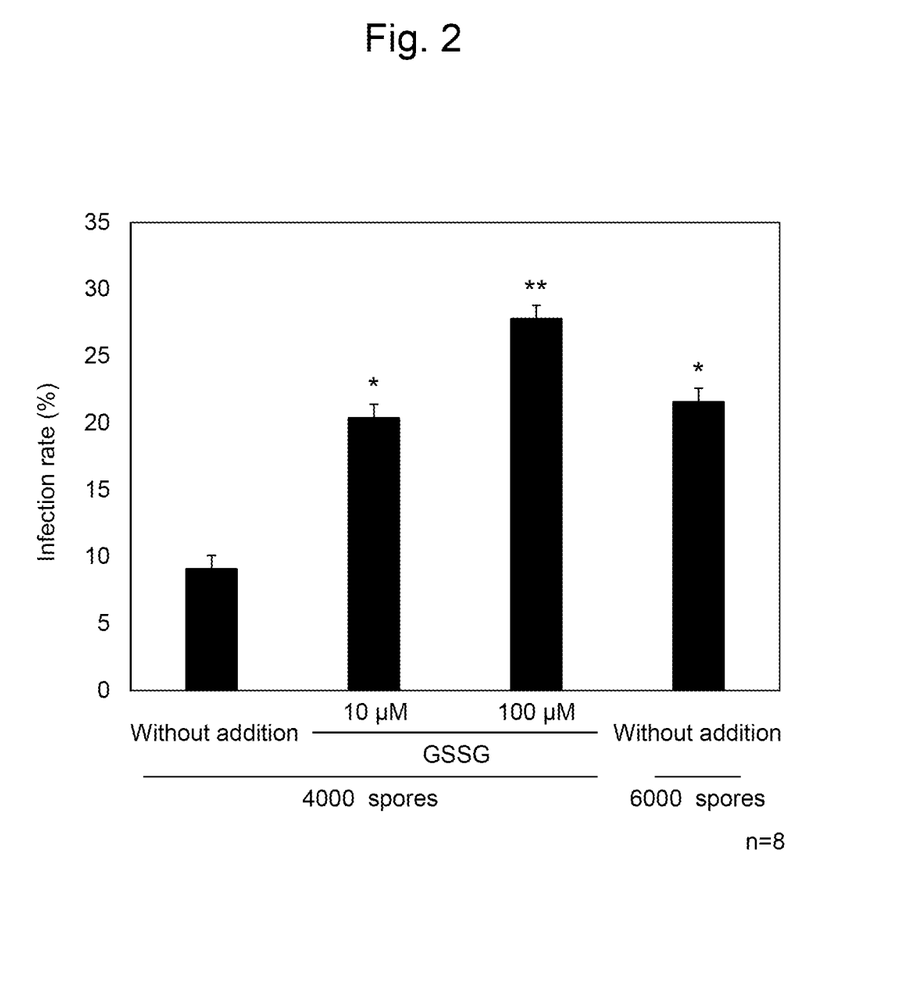
FIG. 2 is a characteristic diagram showing the effects of oxidized glutathione for improving arbuscular mycorrhizal infection with dicotyledonous plants.

The results are shown in FIG. 2. As is apparent from FIG. 2, the infection rate of the plants supplemented with GSSG was significantly enhanced (*p<0.05, **p<0.01, Dunnett's test, n=8), compared with the GSSG-free control plants (4,000 spores). This infection rate is observed to be equivalent at 10 microM and to enhance at 100 microM, compared with the infection rate with the control plants inoculated with the 1.5 times greater amount of spores (6,000 spores). This indicates that effects of promoting host plant infection are observed with the addition of GSSG.

On the basis of the results of Example 2 in combination with the results of Example 1, it was considered that the effects of promoting hyphal elongation of mycorrhizal fungi attained with the addition of GSSG would bring mycorrhizal fungi into contact with host plants more often and enhance the infection rate.

Example 3

In this example, oxidized glutathione was added to soil, monocotyledonous plants were cultivated therein, and the infection rate of arbuscular mycorrhizal fungi was examined.

Specifically, monocotyledonous plants of *Allium* (chives; *Allium schoenoprasum*) were infected with arbuscular mycorrhizal fungi (*Rhizophagus irregularis* DAOM197198), and the infection rate (%) of the mycorrhizal fungi that had invaded inside the roots was determined.

Plants were infected with arbuscular mycorrhizal fungi in the same manner as in Example 2. That is, the medium (one-tenth of the amount, Hoagland No. 2 basal salt mixture (SIGMA), 0.1 mM $KNO_3$) was added to fertilizer-free soil. As control samples, sterilized chive seeds were directly seeded in soil supplemented with spores of arbuscular mycorrhizal fungi (4,000 spores) and in soil supplemented with the spores and GSSG (10 or 100 microM). The plants were allowed to grow at 23 degrees C. with 16-hour light and 8-hour dark cycles for 4 weeks. Thereafter, chives were dug out, the arbuscular mycorrhizal fungi inside the root were stained with ink, and the infection rate of the mycorrhizal fungi (the amount of hyphae per root length (%)) was determined with observation under a microscope.

Figure 3:
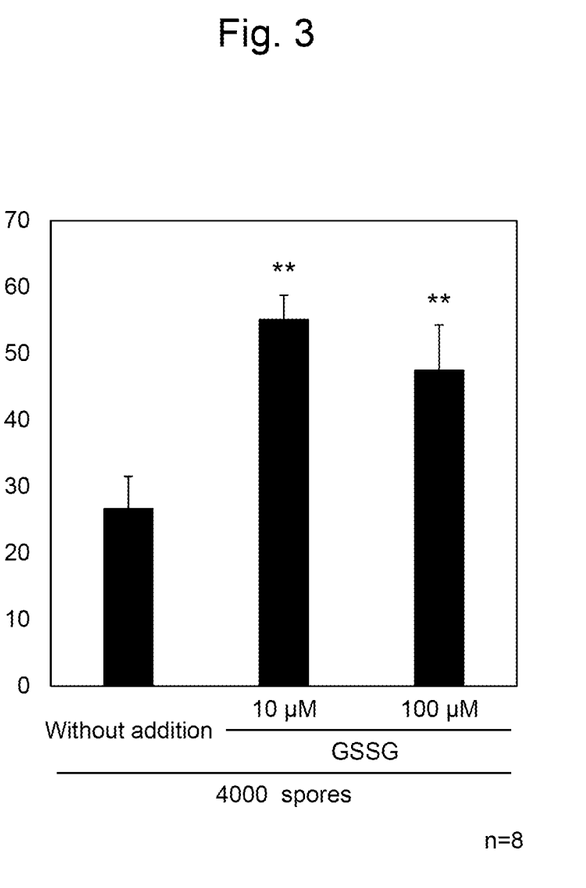
FIG. 3 is a characteristic diagram showing the effects of oxidized glutathione for improving arbuscular mycorrhizal infection with monocotyledonous plants.

The results are shown in FIG. 3. As is apparent from FIG. 3, as with the case of dicotyledonous plants (i.e., *Lotus japonicus*), the infection rate of arbuscular mycorrhizal fungi with monocotyledonous plants (i.e., chives) was found to have significantly enhanced (*p<0.05, **p<0.01, Dunnett's test, n=8) with the addition of GSSG.

Example 4

In this example, the influence of cystathionine instead of oxidized glutathione on the infection rate of arbuscular mycorrhizal fungi was examined.

Chives were used in this example. The medium (one-tenth of the amount, Hoagland No. 2 basal salt mixture (SIGMA), 0.1 mM $KNO_3$) was added to fertilizer-free soil. As control samples, sterilized chive seeds were directly seeded in soil supplemented with spores of arbuscular mycorrhizal fungi (500 or 1,000 spores) and in soil supplemented with the spores and cystathionine (0.1 or 1 mM). The plants were allowed to grow at 23 degrees C. with 16-hour light and 8-hour dark cycles for 4 weeks. Thereafter, chives were dug out, the arbuscular mycorrhizal fungi inside the root were stained with ink, and the infection rate of the mycorrhizal fungi (the amount of hyphae per root length (%)) was determined with observation under a microscope.

Figure 4:
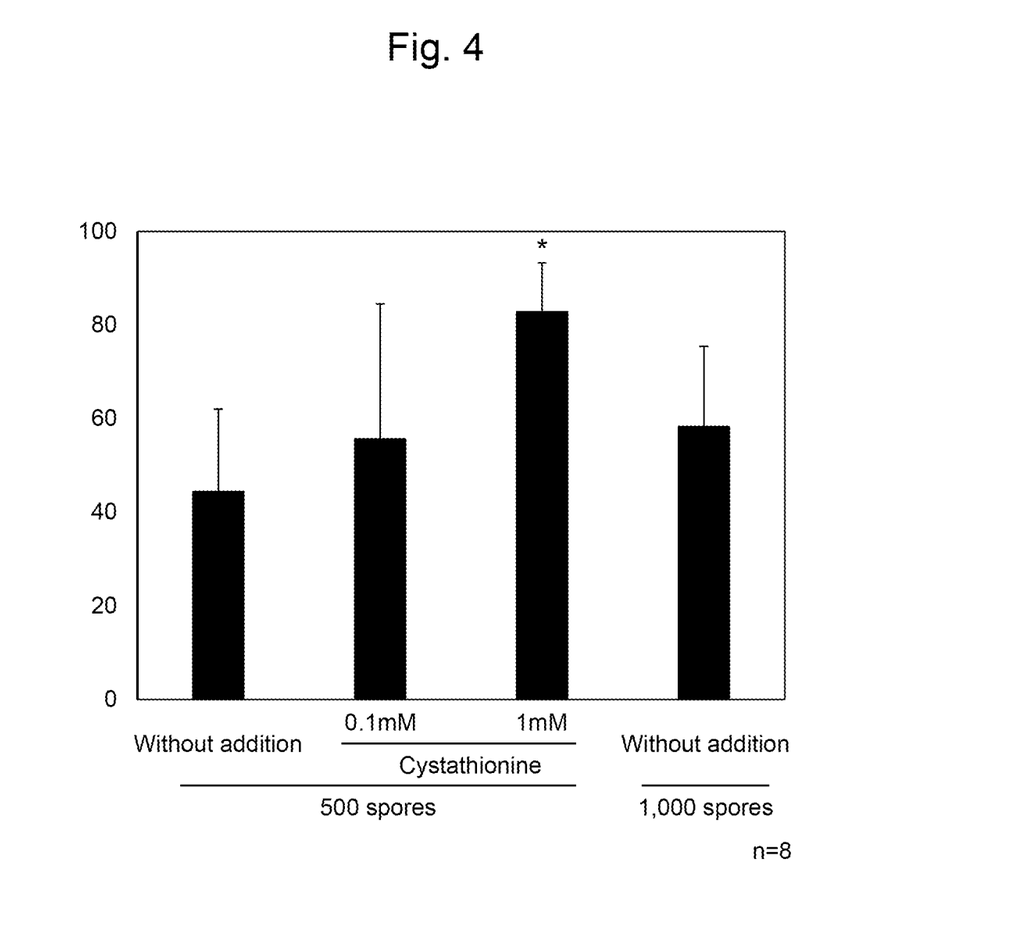
FIG. 4 is a characteristic diagram showing the effects of cystathionine for improving arbuscular mycorrhizal infection with plants.

The results are shown in FIG. 4. As is apparent from FIG. 4, the infection rate was found to have significantly enhanced with the addition of 1 mM cystathionine, compared with the cystathionine-free control sample. The results demonstrate that, as with the case of oxidized glutathione, the effects of infection promotion can be achieved with the addition of cystathionine as an intermediate of glutathione synthesis.

Comparative Example 1

In this comparative example, root nodule bacteria were used instead of arbuscular mycorrhizal fungi, and the influence of oxidized glutathione on root nodule bacterial infection was examined.

Figure 5:
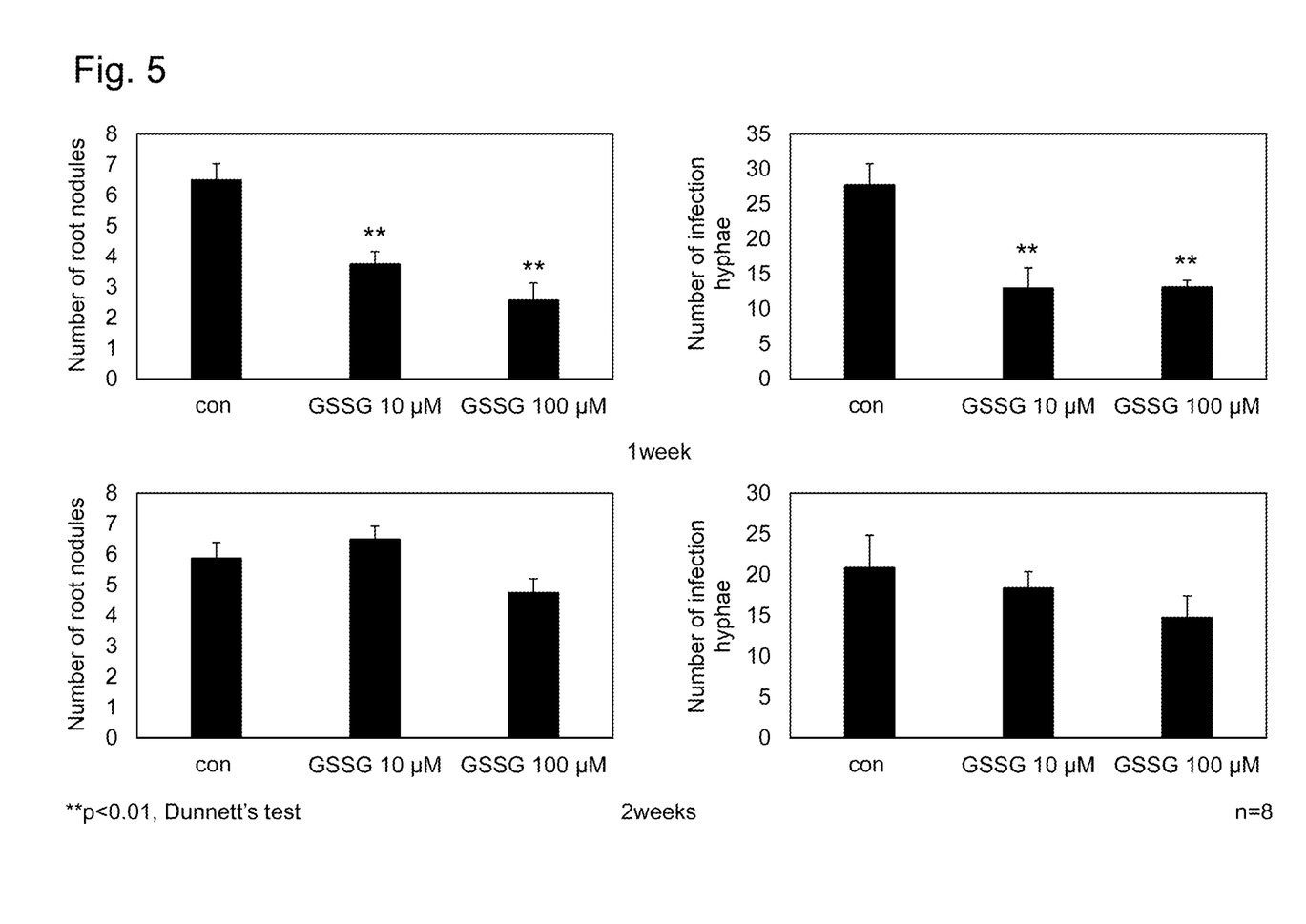
FIG. 5 is a characteristic diagram showing the effects of oxidized glutathione on the number of root nodules and infection hyphae of root nodule bacteria.

In this comparative example, root nodule bacteria from *Lotus japonicus* plants (*Mesorhizobium loti*, a transformant comprising a fluorescent protein (DsRED) introduced thereinto) were used. Vermiculite was supplemented with B&D medium (Broughton and Dilworth, 1971), $KNO_3$ (final concentration: 0.1 mM), root nodule bacteria, and oxidized glutathione at 0, 10, or 100 microM to prepare media. The resulting media (50 ml) were added to 300 ml of fertilizer-free soil (vermiculite) in a pot, and young plants of *Lotus japonicus* 3 days after seeding were planted therein. The infection hyphae that serve as the routes of infection with root nodule bacteria formed in the root hair cells of *Lotus japonicus* and the root nodules that are symbiotic organs formed in the roots of *Lotus japonicus* were examined 1 week and 2 weeks after the growth. The results are shown in FIG. 5. As is apparent from FIG. 5, significant inhibitory effects on formation of both the root nodules and the infection hyphae were observed 1 week after the growth, although such inhibitory effects were not observed 2 weeks after the growth. The results demonstrate that oxidized glutathione is not effective on root nodule bacterial infection or it inhibits root nodule formation.

Comparative Example 2

In this comparative example, reduced glutathione (GSH) and the glutathione-depleting agent (Phoron) were used instead of oxidized glutathione and cystathionine, and the influence of reduced glutathione (GSH) and the glutathione-depleting agent (Phoron) on arbuscular mycorrhizal fungal infection was examined.

In the same manner as in Example 3, the medium (one-tenth of the amount, Hoagland No. 2 basal salt mixture (SIGMA), 0.1 mM $KNO_3$) was added to fertilizer-free soil. As control samples, sterilized chive seeds were directly seeded in soil supplemented with spores of arbuscular mycorrhizal fungi (500 spores and 1,000 spores) and in soil supplemented with the 500 spores, cystathionine (0.1 or 1 mM), GSH (0.1 or 1 mM), and Phoron (0.1 or 1 mM). The plants were allowed to grow at 23 degrees C. with 16-hour light and 8-hour dark cycles for 1 month. Thereafter, chives were dug out, the arbuscular mycorrhizal fungi inside the root were stained with ink, and the infection potential of the mycorrhizal fungi (the amount of hyphae per root length (%)) was determined with observation under a microscope.

Figure 6:
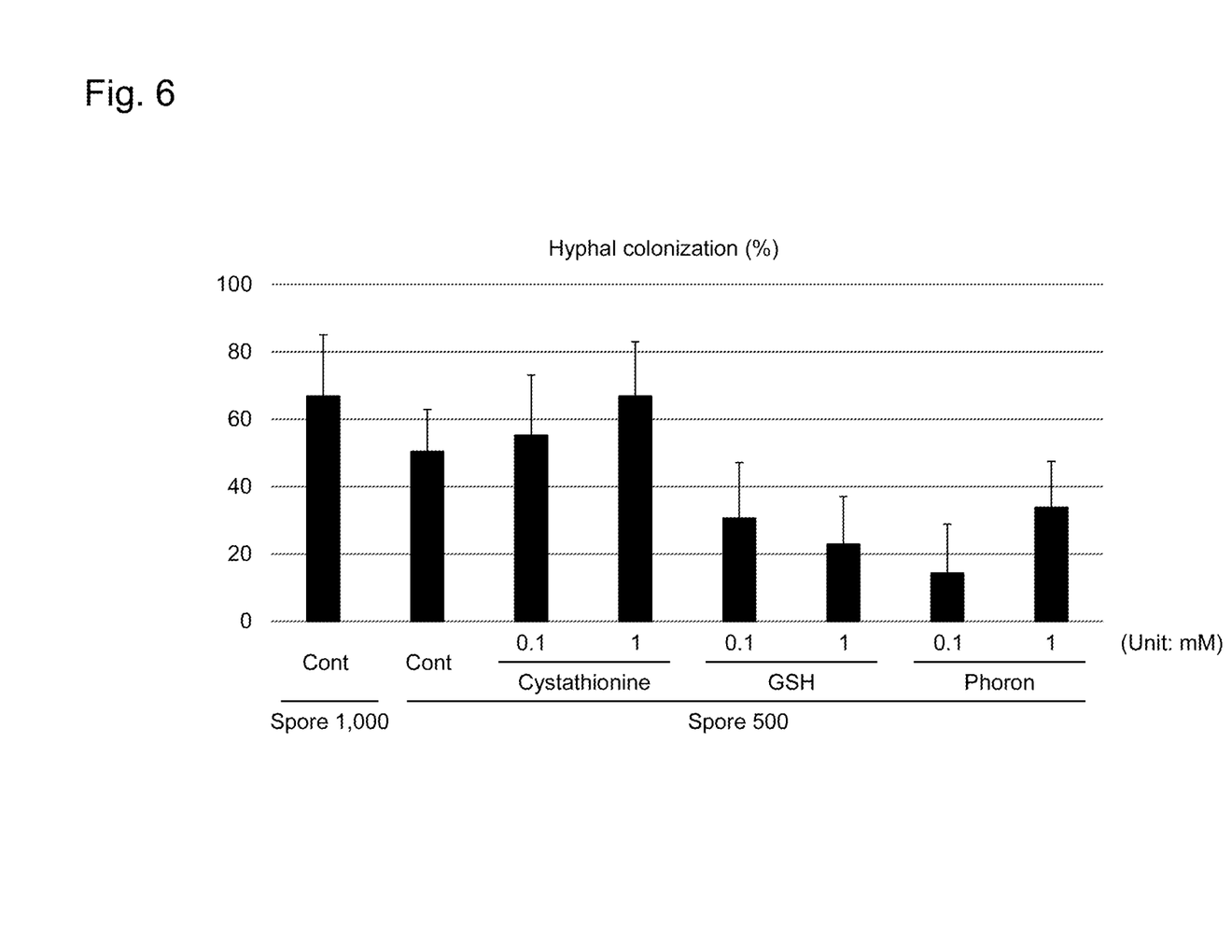
FIG. 6 is a characteristic diagram showing the effects of reduced glutathione and Phoron on the capability for arbuscular mycorrhizal symbiosis.

The results are shown in FIG. 6. As is apparent from FIG. 6, the infection rate was enhanced with the addition of cystathionine, compared with the control sample supplemented with the 500 spores. With the addition of cystathionine at 1 mM, the infection rate was observed to be equivalent to that of the sample supplemented with the 1,000 spores. With the addition of reduced glutathione (GSH), mycorrhizal fungal infection was inhibited. When the glutathione-depleting agent, Phoron, was added, mycorrhizal fungal infection was also inhibited.

Comparative Example 3

In this comparative example, reduced glutathione (GSH) was used instead of oxidized glutathione and cystathionine, and the influence of reduced glutathione (GSH) on hyphal elongation of arbuscular mycorrhizal fungi was examined.

Figure 7:
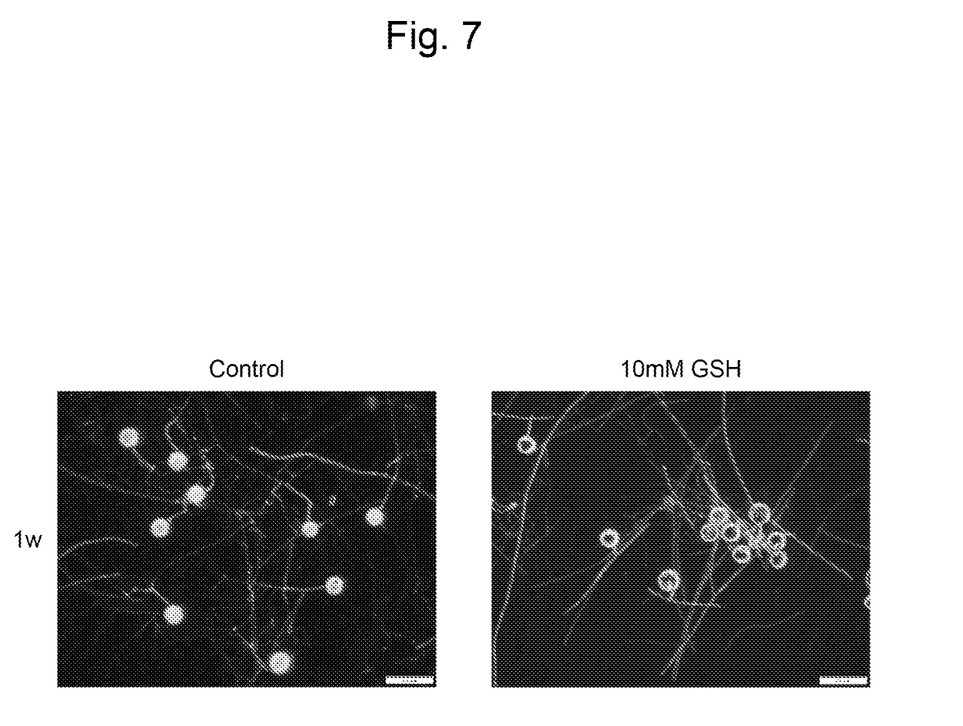
FIG. 7 is a characteristic diagram showing the effects of reduced glutathione on hyphal elongation of arbuscular mycorrhizal fungi.

In the same manner as in Example 1, reduced glutathione (10 mM) was added to the modified M medium (0.3% gerlite), spores of arbuscular mycorrhizal fungi (*Rhizophagus irregularis* DAOM197198) were inoculated therein, and culture was conducted at 30 degrees C. for 1 week. For comparison, arbuscular mycorrhizal fungi were cultured in the same manner, except that reduced glutathione was not added. The results are shown in FIG. 7. As is apparent from FIG. 7, plant growth inhibition, such as deteriorated hyphal elongation of arbuscular mycorrhizal fungi, was observed in the medium supplemented with reduced glutathione (GSH), no hyphal elongation was observed at high concentration (10 mM), and the spores died.

What is claimed is:

1. A microbial material comprising a symbiosis-promoting agent and an arbuscular mycorrhizal fungi, wherein the symbiosis-promoting agent comprises cystathionine and wherein the symbiosis-promoting agent is in contact with the arbuscular mycorrhizal fungi.

2. The microbial material according to claim 1, further comprising a culture medium.

3. The microbial material according to claim 1, wherein the symbiosis-promoting agent comprises a concentration of cystathionine of 100 nM to 100 microM.

4. The microbial material according to claim 1, wherein the symbiosis-promoting agent comprises a salt of cystathionine.

5. The microbial material according to claim 1, wherein the symbiosis-promoting agent causes hyphal elongation of the arbuscular mycorrhizal fungi.

6. The microbial material according to claim 1, wherein contact between the symbiosis-promoting agent and the arbuscular mycorrhizal fungi promotes arbuscule formation in a plant cell.

7. A method for promoting symbiosis for plant cultivation comprising administering the microbial material according to claim 1 to a root of a plant to be cultivated.

8. A method for promoting symbiosis comprising bringing cystathionine into contact with arbuscular mycorrhizal fungi.

9. A method for plant cultivation comprising administering arbuscular mycorrhizal fungi treated with cystathionine to roots of a plant to be cultivated.

\* \* \* \* \*